(12) United States Patent
Cherif-Cheikh et al.

(10) Patent No.: US 8,962,559 B2
(45) Date of Patent: Feb. 24, 2015

(54) SUSTAINED RELEASE FORMULATIONS COMPRISING GNRH ANALOGUES

(75) Inventors: Roland Cherif-Cheikh, Barcelona (ES); Fédéric Lacombe, Barcelona (ES); Maria-Luisa Torres Salgado, Barcelona (ES); Perrine Cambriel, Laroque des Alberes (FR); Mercé Cardus Malaspina, Barcelona (ES); Isabel Diaz Del Consuelo, Barcelona (ES); Martin Montes, Barcelona (ES); Fabien Jeannerot, Versailles (FR); Marie Delporte, Chartres (FR); Anne Brochard, Dreux (FR); Joël Richard, Méré (FR)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 0 days.

(21) Appl. No.: 13/318,320

(22) PCT Filed: Apr. 29, 2010

(86) PCT No.: PCT/IB2010/001303
§ 371 (c)(1),
(2), (4) Date: Apr. 9, 2012

(87) PCT Pub. No.: WO2010/125475
PCT Pub. Date: Nov. 4, 2010

(65) Prior Publication Data
US 2012/0202743 A1 Aug. 9, 2012

(30) Foreign Application Priority Data

Apr. 29, 2009 (EP) .................................... 09290312

(51) Int. Cl.
| | |
|---|---|
| A61K 9/00 | (2006.01) |
| A61K 38/09 | (2006.01) |
| A61K 9/64 | (2006.01) |
| A61K 35/00 | (2006.01) |
| A61P 15/00 | (2006.01) |
| A61P 15/08 | (2006.01) |
| A61P 35/04 | (2006.01) |
| A61K 38/24 | (2006.01) |
| A61L 27/18 | (2006.01) |
| A61L 27/50 | (2006.01) |
| A61L 27/54 | (2006.01) |
| A61L 27/58 | (2006.01) |

(52) U.S. Cl.
CPC ............... *A61K 9/0024* (2013.01); *A61K 38/09* (2013.01); *A61K 38/24* (2013.01); *A61L 27/18* (2013.01); *A61L 27/50* (2013.01); *A61L 27/54* (2013.01); *A61L 27/58* (2013.01); *A61L 2300/25* (2013.01); *A61L 2300/602* (2013.01)
USPC .......................... 514/10.6; 424/400; 427/2.21

(58) Field of Classification Search
None
See application file for complete search history.

(56) References Cited

U.S. PATENT DOCUMENTS

| | | | |
|---|---|---|---|
| 5,916,582 A | 6/1999 | Stevenson et al. | |
| 6,159,490 A * | 12/2000 | Deghenghi | ..................... 424/426 |
| 2006/0029637 A1 | 2/2006 | Tice et al. | |
| 2008/0063687 A1 | 3/2008 | Chou et al. | |

FOREIGN PATENT DOCUMENTS

| | | | | |
|---|---|---|---|---|
| JP | 2001-504442 | | 4/2001 | |
| WO | 98/00157 | | 1/1998 | |
| WO | WO 00/33809 | * | 6/2000 | ............... A61K 9/00 |
| WO | WO 03/094888 | | 11/2003 | |
| WO | WO 2005/000278 | * | 1/2005 | ............... A61K 9/22 |
| WO | WO 2005/000278 A1 | * | 1/2005 | ............... A61K 9/22 |
| WO | WO 2005/082418 | | 9/2005 | |
| WO | WO 2006/130703 | | 12/2006 | |
| WO | WO 2009/051819 | | 4/2009 | |

OTHER PUBLICATIONS

Smith, Katie. "Triptorelin & GnRH Analogues Review" (Nov. 2007) London New Drugs Group—16 pages.*
ISR for PCT/IB2010/001303 mailed Jun. 23, 2011.
Written Opinion for PCT/IB2010/001303 mailed Oct. 29, 2011.
International Preliminary Report on Patentability for PCT/IB2010/001303 for Nov. 1, 2011.
Lemay *Horm. Res.* 1989 32(Suppl. 1): 93-102.

* cited by examiner

*Primary Examiner* — Jean Witz
*Assistant Examiner* — Mindy Newman
(74) *Attorney, Agent, or Firm* — Hunton & Williams LLP

(57) ABSTRACT

The present invention relates to pharmaceutical compositions for the controlled and sustained release of active substance comprising a biodegradable polymer or copolymer. Furthermore, the invention relates to pharmaceutical compositions for the controlled and sustained release of at least one active substance such as peptides or hormones and analogs thereof and the manufacturing process of such pharmaceutical compositions.

33 Claims, 6 Drawing Sheets

SUSTAINED RELEASE FORMULATIONS COMPRISING GNRH ANALOGUES

This application is a national stage filing of PCT/IB2010/001303, filed Apr. 29, 2010, the subject matter of which is incorporated herein in its entirety. This application further claims priority to EP 09290312.9, filed Apr. 29, 2009, the subject matter of which is incorporated herein in its entirety.

The present invention relates to pharmaceutical compositions for the controlled and sustained release of active substance comprising a biodegradable polymer or co-polymer. Furthermore, the invention relates to pharmaceutical compositions for the controlled and sustained release of at least one active substance such as peptides or hormones and analogues thereof and the manufacturing process of such pharmaceutical compositions.

More particularly, the invention relates to pharmaceutical compositions in the form of small implants which comprise at least one active substance such as the gonadotropin-releasing hormone (GnRH) analogues such as triptorelin or salts thereof in a polymer or co-polymer sleeve.

GnRH, also known as LHRH, is a decapeptide hormone responsible for the secretion of follicle-stimulating hormone (FSH) and luteinizing hormone (LH). GnRH analogues are synthetic peptide drugs modelled after GnRH. Analogues may be either agonists or antagonists. Agonists activate the GnRH receptor resulting in increased release of FSH and LH. Antagonists, on the other hand, block the GnRH receptor, reducing the release of FSH and LH.

Triptorelin also known as [D-Trp$^6$] LHRH, is the active ingredient in the medicament DECAPEPTYL® and may be used to treat diseases including prostate cancer, in particular advanced metastatic prostate cancer, endometriosis, female infertility and is usually associated with other hormones in the course of in-vivo fertilisation (IVF), precocious puberty; fibroids and endometriosis.

Peptides such as GnRH analogues are usually administered parenterally, for example by subcutaneous injection. One reason for this is that they are usually degraded in the gastrointestinal tract. GnRH analogue treatments require either the continuous or repeated administration to the patient over an extended period of time.

However, repeated injections cause both inconvenience and discomfort to the patient. Sustained-release formulations have been developed to deliver GnRH analogues over prolonged periods of time without the need for repeated injections. Such formulations have added benefits including increasing dosage accuracy and assurance of patient compliance.

An underlying problem with many existing formulations sustained release over an extended period is not contemplated in the prior art. Significantly, many GnRH analogue treatments require administration to the patient for six months or more.

The preparation of many existing formulations is relatively complex in that the corresponding procedures require the addition of one or more excipients, or additional steps such as heat fusion and compression moulding.

Additional excipients are often required for homogeneity, stabilisation and to improve mouldability or solidify the mixture therefore, it would be advantageous if the desirable properties could be obtained without the need to add excipients.

Heat fusion and compression moulding may be employed to arrange the active ingredient in the core. Compression moulding may be necessary as the mixture is transformed into a solid before it is introduced into the core. A problem with methods of production involving these steps is that it is relatively complex, rendering industrialisation difficult.

International patent publication number WO 2005/117934 discloses a sustained release apparatus including at least one implant. The implant includes a support material and a pharmaceutical composition including a luteinising hormone releasing hormone (LHRH) agonist and/or antagonist component. The implant may have a double layer structure, with the outer layer formed of a silicone material. The implant having an open end at one terminal may be fabricated by dipping one terminal of the formulation into a solution to dissolve the outer-layer material.

The use of silicon may suffer from a disadvantage in that it does not degrade after administration. This may adversely effect the release profile of the LHRH agonist and/or antagonist component and result in undesirable silicon waste material remaining in the subject after the completion of the release.

European patent number 1001743 discloses a core containing an active principle and a sheath which fully surrounds the core. Having a sheath which fully surrounds the core reduces performance in that the level of the active ingredient released soon after administration is low due to the sheath blocking the release. Such implants also suffer from a second disadvantage in that the process for their manufacture is relatively complex.

U.S. Pat. No. 5,851,547 discloses a controlled release drug formulation which comprise an inner layer which swells and an outer layer which is impermeable to water and which controls the swelling of the inner layer. The drug is released exclusively through at least one open end of the inner layer and the inner layer is non-disintegrating in that it retains its original shape for the period of time over which the drug is released. A problem with such formulations is that the release of the drug is governed solely by one parameter: the amount of the drug that can be released through the open end. This is a consequence of the inner layer being non-disintegrating, and it limits the period of release.

In one particular aspect, the invention is suitable for providing the controlled and sustained release of the GnRH analogue triptorelin from a poly(lactide-co-glycolide) acid (PLGA) coated with a biodegradable polymer or co-polymer sleeve.

It is therefore an object of the present invention to provide a method which alleviates at least one disadvantage by providing, for example:
  extended release,
  improved release control,
  more complete release,
  a relatively simple manufacture process, and/or
  improved biodegradability.

In one aspect, the invention provides an elongated implant for the controlled and sustained release of at least one GnRH analogue, the implant comprising
  a polymer or co-polymer sleeve and,
  in the sleeve, a polymeric or co-polymeric core comprising
    at least one GnRH analogue,
characterised in that
  at least one end of the sleeve is open, and
  the sleeve degrades during the sustained release.

In another aspect, the invention provides a process for the preparation of an elongated implant, comprising the steps of
  preparing a biodegradable polymeric or co-polymeric sleeve,
  combining a GnRH analogue and a polymer or copolymer to form a polymeric or co-polymeric core, and subsequently,
  placing the core in the sleeve.

In a further aspect, the invention provides an elongated implant for the controlled and sustained release of the GnRH analogue triptorelin acetate, the implant comprising
   a polymeric or co-polymeric sleeve having at least one open end, and
   in the sleeve, a core comprising the triptorelin acetate.

In yet another aspect, the invention provides a process for the preparation of an elongated implant, comprising the steps of
   preparing a polymeric or co-polymeric sleeve,
   preparing a solution of between 40 and 80% (w/w) triptorelin acetate in water,
   placing the solution in the sleeve,
   incubating the solution for 2-48 h at 20-30° C., and
   drying for 6-24 h under vacuum.

In yet another aspect, the invention further provides a process for the preparation of an elongated implant by "twin extrusion", comprising the steps of:
   introducing pellets made of biodegradable polymer or copolymer and active substance in the core extruder
   extruding the core made of biodegradable polymer or copolymer and active substance (GnRH analogue) and after cooling
   coating with a biodegradable polymer or copolymer.

Figure 1:
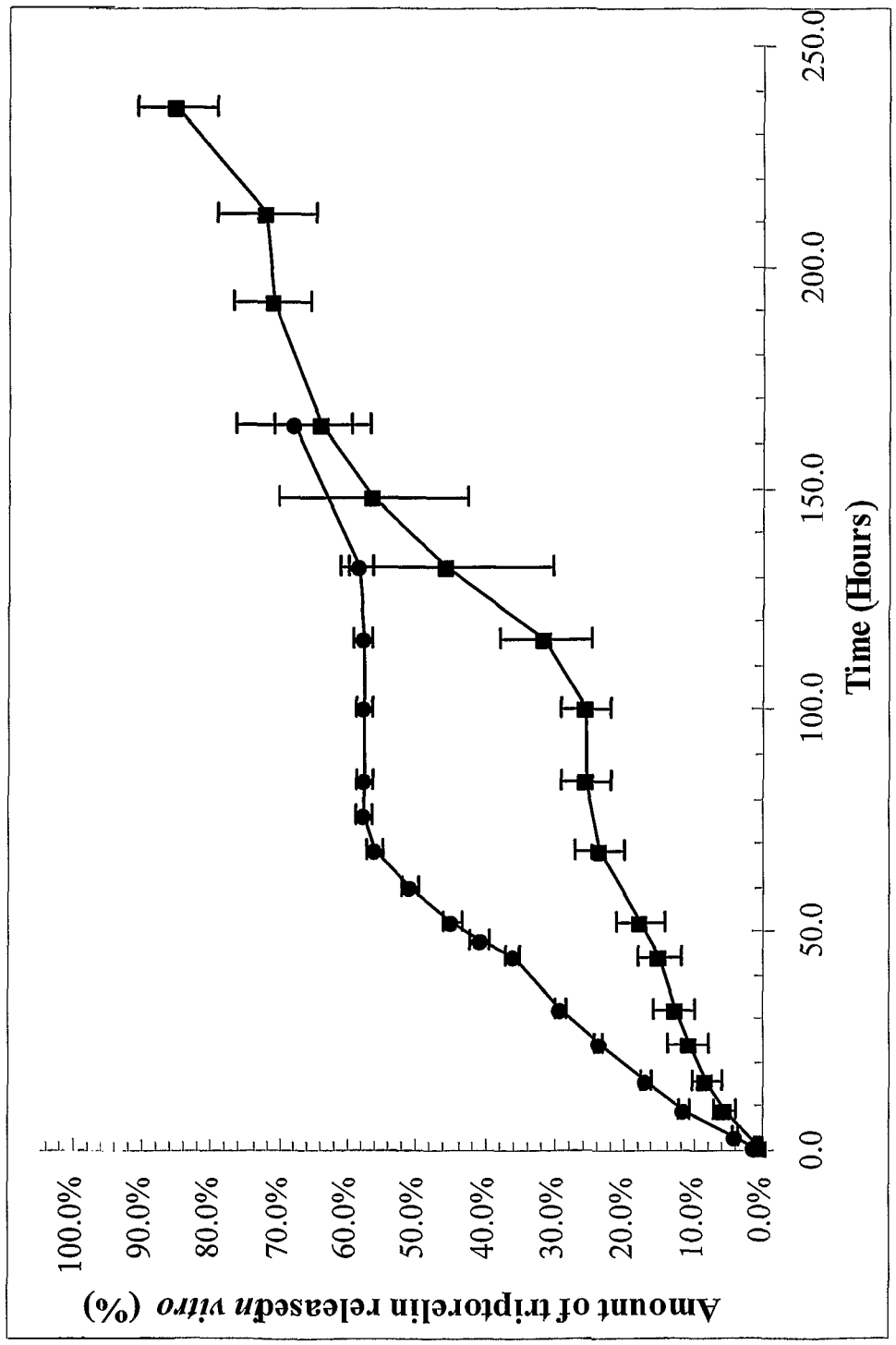
FIG. 1: compares the in vitro dissolution profiles of an implant comprising a polymeric core of triptorelin acetate and PLGA in a polymeric sleeve of PLGA prepared according to Example 5 (represented by filled squares) and a polymeric core of triptorelin acetate and PLGA prepared according to Example 2 (represented by filled circles).

The following definitions are set forth to illustrate and define the meaning and scope of the various terms used to describe the invention herein.

The term "controlled and sustained release" as used herein means release of the active substance in a patient such that the patient receives an effective dose of the active substance over a time period of at least one month.

When used with reference to GnRH, "analogue" means a naturally occurring, recombinant or synthetic peptide, or a derivative or fragment of peptides, that exhibits substantially the same agonist or antagonist effect as unmodified, or naturally occurring peptides.

The term "conformational change" with reference to conformational changes of triptorelin acetate means a change in spatial conformation of the triptorelin acetate when mixed with the water. The change may be induced for example by change of temperature or concentration.

The term "twin extrusion" means the production on the same production line of a cylindrical central body or core made of co-polymer and or active pharmaceutical ingredient (API) and a tubular polymer coating or shell deposited on the core after its solidification.

Suitable GnRH analogues for the compositions disclosed in the present invention include leuprorelin, buserelin, nafarelin, histrelin, goserelin, deslorelin, gonadorelin, avorelin, triptorelin, and their salt forms.

According to the present invention preferably GnRH analogue is used as a triptorelin salt. More preferably, the GnRH analogue is triptorelin acetate or triptorelin pamoate. Even more preferably, GnRH analogue is triptorelin acetate.

In the present application, "triptorelin acetate" means an acetate salt form of triptorelin which contains more than 95% by weight pure triptorelin acetate, and preferably more than 97 or 98% by weight pure triptorelin acetate. This corresponds respectively to a percentage of approximately 80, 84 or 85% by weight of pure triptorelin.

According to the invention, when the GnRH analogue is triptorelin acetate, the amount of triptorelin acetate in the polymeric core is within the range of 30 to 90% by weight relative to the total weight of the polymeric core. Preferably, the amount of triptorelin in the polymeric core is within the range of 35 to 65% by weight relative to the total weight of the polymeric core.

In a further aspect of the present invention, the sustained release of the active substance can occur via at least two mechanisms, which enables improved control over the release. Firstly, the hormone analogue may be released via the at least one open end of the sleeve. Secondly, the hormone analogue may be released through the sleeve, as the sleeve and the core degrade. The elongated implant may include a void between the sleeve and the core which may assist in the sustained release.

Said polymers or co-polymers are preferentially used in a form which is purified or devoid of the residual monomer fraction. Polymers or co-polymers of this type are for example described in U.S. Pat. No. 4,728,721.

According to a preferred variant of the invention, the polymeric or co-polymeric core is in the form of a cylinder with a small diameter, preferably less than 1.5 mm, more preferably less than 1 mm, and even more preferably between 0.6 and 0.9 mm.

Preferably, the polymer or co-polymer is formed from lactic acid and/or glycolic acid. More preferably, the polymer or co-polymer is polylactic acid (PLA), a polymer formed from lactic acid. Even more preferably, the polymer or co-polymer is poly(lactic-co-glycolic acid), which is a co-polymer of lactic acid and glycolic acid.

The co-polymer PLGA degrades by hydrolysis of its ester linkages in the presence of water. The time required for degradation of PLGA polymer generally depends on the ratio of the monomers used for its production, with a higher proportion of lactic acid units resulting in an increase in the time required for degradation.

According to the invention the ratio of lactic acid to glycolic acid in the PLGA is within the range of 70:30 to 90:10. Preferably, the ratio of lactic acid to glycolic acid in the PLGA is 85:15. A ratio of lactic acid to glycolic acid in the PLGA of, 85:15, for example, indicates a PLGA polymer comprising 85% units derived from lactic acid and 15% units derived from glycolic acid. Pure lactic acid polymers may also be employed, and are particularly suitable for release periods of more than three months.

Preferably, the polymeric or co-polymeric sleeve and the polymeric or co-polymeric core are made from the same polymer or co-polymer. The polymeric or co-polymeric sleeve and the polymeric or co-polymeric core may both be made from PLGA made with a ratio of lactic acid to glycolic acid of 85:15.

When the polymer or co-polymer comprises PLGA, it preferably has a molecular mass of at least 60 kDa. More preferably, the PLGA has a molecular mass of at least 100 kDa. Most preferably, the PLGA has a molecular mass within the range of 120 kDa to 170 kDa. When the polymer comprises PLA, the PLA will preferably have a molecular mass comprised between 15 kDa or 20 kDa and 30 kDa or 40 kDa, or more preferably 25 kDa.

The implant is suitable for the release of the GnRH analogue for a duration of at least 3 months, preferably for a duration of at least 6 months.

When the GnRH analogue comprises triptorelin acetate, it is preferably present in an amount within the range of 0.5 to 50 mg. More preferably the triptorelin acetate is present within the range of 2 to 20 mg. Most preferably, the triptorelin acetate is present in an amount of approximately 5, 6, 7, 8, 9 or 10 mg.

In addition the axial length of the implant is between 1 and 4 cm. Preferably, the axial length of the implant is between 2 and 3 cm. More preferably, the axial length of the implant is approximately 2.5, 2.6, 2.7 or 2.8 cm. Most preferably, the axial length of the implant is 2.6 cm.

Preferably, the external diameter of the elongated implant is comprised within the range of 0.70 mm to 1.2 mm, more preferably within the range of 0.80 mm to 1.1 mm. Even more preferably, the external diameter of the elongated implant is 0.85, 0.90, 0.95, 1.0 or 1.1 mm.

Preferably, the ratio of the diameter to axial length of the implant is between 1:20 and 1:40. More preferably, the ratio of the diameter to axial length of the implant is between 1:22 and 1:30. Even more preferably, the ratio of the diameter to axial length of the implant is 1:23, 1:25, 1:28 or 1:30.

The optimum size of the implant may be determined having regard to the volume of the dose to be included and the increased discomfort to the patient that is associated with increased implant size.

Furthermore, the percentage of the GnRH analogue released from the elongated implant during the sustained release is more than 60%. Preferably, more than 80% of the GnRH analogue in the form of triptorelin acetate is released from the elongated implant during the sustained release. More preferably, more than 90% of the triptorelin acetate is released from the implant during the sustained release. Most preferably, 100% of the triptorelin acetate is released from the implant during the sustained release.

In yet another aspect, the invention relates to a method for treating a patient in need of regular administration of at least one GnRH analogue, said method consisting of administering an implant described above into the patient by injection.

As previously mentioned, in a further aspect, the invention provides a process for the preparation of an elongated implant, comprising the steps of
preparing a biodegradable polymeric or co-polymeric sleeve,
combining a GnRH analogue and a polymer or co-polymer to form a polymeric core, and
subsequently, placing the core in the sleeve.

This aspect of the invention has the advantage of improved simplicity by avoiding addition of excipients other than PLGA to the hormone analogue.

The polymeric sleeve and the polymeric core may be prepared, for example, by extrusion or moulding. Preferably the polymeric sleeve and the polymeric core are prepared by melt extrusion. Preferably, the first step in the preparation of the polymeric sleeve and the polymeric core is the extrusion of PLGA to form pellets. The extrusion to form the pellets preferably occurs at a temperature between about 130±10° C. to 155±10° C. preferably at 145±10° C. and at rotation rate of the extruder of about 25±10 rpm to 45±10 rpm preferably at 35±10 rpm. The resulting pellets may then be milled, for example with a cryogenic mill, to form a powder. The powder size is preferably less than 1 mm, and more preferably less than 500 µm.

Preferably, the sleeve is prepared by extruding the pellets of polymer. This extrusion preferably occurs at a temperature within the range of 130 to 160° C., more preferably 142 to 156° C. The rotation rate of the extruder is preferably between 1 and 30 rpm, more preferably 2 and 6 rpm, and most preferably 4 rpm.

In order to prepare the polymeric core, the powder and the GnRH analogue may be combined by mixing, preferably for about 30 minutes at 42 rpm. The formation of the polymeric core from the powder preferably occurs in two extrusions. In the first extrusion, the mixture was extruded at a temperature preferably within the range of 110 to 130° C., more preferably 116 to 124° C., and most preferably about 120° C., to form pellets. The rotation rate of the extruder is preferably between 1 and 40 rpm, more preferably 15 and 25 rpm, and most preferably 21 rpm. The first extrusion improves the flow properties of the blend, enabling a constant feeding rate during the second extrusion and hence an extrudate of uniform diameter.

The residual moisture in the pellets of triptorelin acetate and PLGA resulting from the first extrusion is preferably less than 5% by weight of water relative to the total weight. However, the precise moisture content depends on the proportion of GnRH analogue, which is the main source of moisture. In this regard, the residual moisture in pellets resulting from the first extrusion is more preferably less than approximately 1.5% when the triptorelin concentration is approximately 35% and less than approximately 2% when the triptorelin concentration is approximately 50%. The pellets are preferably dried under vacuum before the second extrusion, in order to reduce the water content below the desired limit.

After drying, the pellets may undergo the second extrusion at a temperature preferably within the range of 120 to 160° C., more preferably 130 to 150° C., and most preferably about 140° C.

The molten or liquefied state of the peptide in the polymer allows mixing without the need for expensive pre-treatments using production vehicles which would have to be subsequently eliminated.

The temperature can be adapted as a function of the polymer or co-polymer used; it will for example be approximately 10° C. lower in the case of an approximately PLGA with lower inherent viscosity or approximately 10° C. higher for a PLGA with a higher viscosity.

According to this variant of the polymeric core production process, the operation is carried out without pre-treatment of the mixture using aqueous or organic solvents, which would need to be subsequently eliminated. The process also avoids the need for lyophilization of the mixtures and distinct pre-heating for compression before extrusion.

The solid mixture of triptorelin acetate powder and PLGA polymer can be melted at a sufficient temperature in order to obtain a non-solid state of the two constituents to then be mixed and then extruded or moulded before lowering the temperature and returning the arrangement to the solid state.

The extrusion machine can operate at ambient temperature at the extruder outlet.

This continuous extrudate can then be cut to give polymeric cores of appropriate size. The desired dose can thereby be obtained before the polymeric core is placed into the sleeve.

Depending on the form, dose and desired release profile, the production process of the polymeric core can also be applied to forms with small loadings of active ingredient. The indications given above in terms of residual moisture and quantity of active ingredient as well as of the nature of the polymer, for example, can be applied to compositions having loadings of less than 50% as well as those having loadings greater than this value. The adaptations necessary are within the scope of a person skilled in the art considering the indications given above as well as in the production examples.

In an embodiment, the dimensions of the polymeric sleeve and polymeric core are verified and the core placed in the sleeve by hand or mechanically. The implant may then be placed into an injection device and gamma-irradiated before administration.

Depending on the size of the implant, the attending doctor can use injection devices such as those described in the PCT Application WO 2006/058745 or syringes of standard size in order to carry out the administration.

A person skilled in the art can choose to use other polymers or also a mixture of polymers, or to have other proportions of triptorelin salt and PLGA polymer; in this case, the molecular mass of the PLGA polymer and the weight of the polymeric core will be adapted in order to obtain the desired release profile.

In a further aspect, the invention provides a process for the preparation of an elongated implant, comprising the steps of
  combining a GnRH analogue and a polymer or co-polymer, and
  subsequently, co-extruding the combination and a biodegradable polymer or co-polymer,
  to form an implant comprising a GnRH analogue and polymeric or co-polymeric core inside a biodegradable polymeric or co-polymeric sleeve.

Preferably, when the GnRH analogue and polymer are combined, pellets are formed.

The co-extrusion temperature and extrusion speed may be selected based on the softening point of the combination forming the core and the polymer forming the sleeve. Preferably, the co-extrusion takes place under the conditions identified above for the single extrusions.

In another aspect, the invention provides the implant described above, obtainable according to the process described above.

The invention provides another process for the preparation of an elongated implant, comprising the step of
  introducing pellets made of biodegradable polymer or copolymer and active substance in the core extruder
  extruding the core made of biodegradable polymer or copolymer and active substance and thereafter cooling
  coating with a biodegradable polymer or copolymer.

The distance between the extrusion head and the coating/deposition head may be increased and the melting gutter is placed after the core extrusion head in order to cool and solidify the core before entering in the channel of the coating equipment.

The position between the core extrusion head and the coating/deposition is optionally adjusted around 130 mm to 160 mm preferably around 150 mm to obtain a core shell implant. The distance chosen may control the cooling period According to the process, the adhesion of core and shell could be controlled by process parameters such as temperatures, speed of extrusion and coating. Adjustment of these parameters may create a permanent bonding or a looser fitting enabling the presence of a small air gap between core and shell.

The final product obtained by this process is a cylindrical elongated implant consisting of a core made of a blend of copolymer and active substance, and a shell. The shell is made of pure polymer or copolymer and is optionally of the same or different nature. and composition as the copolymer used for the core.

The finished product obtained is a core covered with a transparent coating: the two parts form an integral product.

In this aspect of the invention and by the way of this process it is possible to obtain structured implants similar to those obtained by the manual insertion of cylindrical core into the tube.

The valuable advantage of the process as above described does not need any manual assembly of the core implant into the shell.

As previously mentioned, in a further aspect, the invention provides an elongated implant for the controlled and sustained release of the GnRH analogue triptorelin acetate, the implant comprising
  a polymeric or co-polymeric sleeve having at least one open end, and
  in the sleeve, a core comprising the triptorelin acetate.

Preferably, the triptorelin acetate undergoes a conformational change which increases the viscosity of the core.

Preferably, the sleeve degrades during the release.

The polymeric sleeve may be prepared in accordance with the method described above.

Preferably, the content of water in the elongated implant of this aspect of the invention is less than 1%.

Preferably, gel of triptorelin acetate and water is introduced directly into the sleeve and therefore the process may avoid the need for moulding or extrusion of the core.

In an embodiment of the method of the invention, at least 40% of triptorelin acetate is mixed with water and placed into the sleeve. Preferably, at least 50 or 60 or 70 or 80 or 90% of triptorelin acetate is mixed with water and placed into the sleeve.

Preferred methods for the preparation of the core commence with the mixing of 40 to 80% (w/w) triptorelin acetate and water, preferably 50 to 70% (w/w) triptorelin acetate, or more preferably 55, 60 or 65% (w/w) triptorelin acetate. The preferred triptorelin acetate concentration allows for sufficient triptorelin acetate content in the final elongated implant.

In one preferred method, the water and triptorelin acetate are placed in separate containers connected via a valve and a vacuum created in the container housing the triptorelin acetate. Opening the valve results in the water entering the container housing the triptorelin acetate and filling the gaps within the powder of triptorelin acetate. The gel formed by water and triptorelin acetate may then be homogenised.

In an alternative preferred method, the triptorelin acetate and water are mixed by gentle agitation.

Preferably, the water used in the preparation of the core is in the form of water for injection.

Temperature during mixing of triptorelin acetate and water is preferably maintained below 25° C. more preferably below 15° C. and even more preferably between 5 and 10° C. Maintaining a relatively low temperature delays crystallization or conformational change.

The triptorelin acetate and water may then be conveniently placed into the sleeves.

Once the semisolid is inside the tube, the gel may undergo a conformational change and is crystallised.

The first step of this two step process may involve incubation for 2-48 hours at 20° C.-40° C. preferably at 20-30° C. and atmospheric pressure to produce a semisolid composition of triptorelin acetate and water. The incubation of the core may produce a conformational change in the triptorelin acetate. Solidifying the composition in this manner facilitates the retention of the composition within the sleeve and makes it easier to dry the composition in the second step.

The second step may include drying for 6 to 24 hours at room temperature under vacuum to reduce the water content.

In an embodiment, the implant may be placed by hand in the device for administration by injection. The implant and device is preferably exposed to gamma-irradiation before administration by injection. Alternatively, terminal sterilisation may be avoided by producing the implants in aseptic conditions.

In yet another aspect, the invention relates to a method for treating a patient in need of regular administration of at least one GnRH analogue, said method consisting of administering an implant described above into the patient by injection.

Pharmaceutical compositions according to the invention will be used by parenteral way such as subcutaneous or intramuscular injection.

Preferably administration of the pharmaceutical composition as elongated implant containing 6, 9 or 10 mg of triptorelin acetate is by way of a subcutaneous injection repeated every 6 months.

Preferably, the use of triptorelin in an elongated implant as disclosed in the present invention is adapted to treat diseases including prostate cancer, in particular advanced metastatic prostate cancer, endometriosis, female infertility and is usually associated with other hormones in the course of in-vivo fertilisation (IVF), precocious puberty; fibroids and endometriosis.

All the publications, patent applications, all patents and all other references mentioned here are incorporated by way of reference.

The following examples serve as illustrations of the invention without limiting it.

EXAMPLE 1

Polymeric Core Manufacture Method

Examples 1 to 11 relate to the preparation of implants according to the invention, comprising a polymeric core of triptorelin acetate and PLGA in a polymeric tubular sleeve of PLGA.

For use in the preparation of both sleeves and polymeric cores, PLGA underwent an initial preparation step. The step involved extruding the PLGA at 145±10° C. and 35±10 rpm and milling the resulting pellets in a cryogenic mill, to form a PLGA powder having a particle size of less than 500 μm for implants manufacturing.

In order to produce the polymeric core, GnRH analogue in the form of triptorelin acetate and the PLGA powder were consecutively weighed. The triptorelin acetate was passed through a sieve to avoid the presence of lumps in the mixture. The blend was then mixed for 30 min, and then extruded at 120±4° C. and 21±1 rpm.

The pellets were dried under vacuum before the second extrusion to reduce the water content below 2% or 1.5%. The granules were melt-extruded at 138±2° C. and 9±2 rpm.

The extrudate was cut during the second extrusion and the individual polymeric cores were obtained.

EXAMPLE 2

Polymeric Core Manufacture Results

A polymeric core was manufactured according to the general procedure outlined in Example 1.

The polymeric core contained a dose of 6 mg, measured 0.85 mm in diameter and approximately 26 mm in length and comprised 40% by weight of triptorelin acetate (purity≥97.5%) and 60% by weight of 85:15 PLGA (inherent viscosity iv in chloroform: 1.2 dl/g≤iv≤1.7 dl/g).

EXAMPLE 3

Polymeric Sleeve Manufacture Method

In order to produce the sleeve, PLGA powder having undergone the initial preparation step outlined in Example 1 was melt-extruded at 149±7° C. and 4±2 rpm and the extruded tube was cut to obtain the sleeves.

EXAMPLE 4

Polymeric Core in Polymeric Sleeve Manufacture Method

A large number of polymeric cores and polymeric sleeves were prepared according to Examples 1 and 3, respectively. The dimensions of the polymeric cores and sleeves were verified and the cores were placed in the sleeves. The resulting implants were placed into an injection device and gamma-irradiated above 25 kGy before administration.

EXAMPLE 5

Polymeric Core in Polymeric Sleeve Manufacture Results 1

Implants prepared according to Example 4 were selected, having the properties set out in Table 1, below.

TABLE 1

| | 5.9 mg triptorelin acetate polymeric core in 1.1 mm sleeve | |
|---|---|---|
| Sleeve | Sleeve Length (mm) | 26.0 |
| | Sleeve External Diameter (mm) | 1.10 |
| | Sleeve Internal Diameter (mm) | 0.82 |
| Core | Triptorelin Acetate Content (mg/mg) | 0.342 |
| | Mean Dose (mg) | 5.9 |
| | Mean Purity (%) | 97.3 |
| | Implant Core Loading in Triptorelin Acetate (%) | 40.2 |

EXAMPLE 6

Polymeric Core in Polymeric Sleeve Manufacture Results 2

Six implants prepared according to Example 4 were selected, having the properties set out in Table 2, below.

TABLE 2

| | 6.4 mg triptorelin acetate polymeric core in 0.85 mm sleeve | |
|---|---|---|
| Sleeve | Sleeve Length (mm) | 26.1 |
| | Sleeve External Diameter (mm) | 0.85 |
| | Sleeve Internal Diameter (mm) | 0.65 |
| Core | Triptorelin Acetate Content (mg/mg) | 0.597 |
| | Mean Dose (mg) | 6.4 |
| | Mean Purity (%) | 97.6 |
| | Implant Core Loading in Triptorelin Acetate (%) | 70.3 |

EXAMPLE 7

Polymeric Core in Polymeric Sleeve Manufacture Results 3

Six implants prepared according to Example 4 were selected, having the properties set out in Table 3, below.

TABLE 3

| | 9.1 mg triptorelin acetate polymeric core in 1.1 mm sleeve | |
|---|---|---|
| Sleeve | Sleeve Length (mm) | 26.0 |
| | Sleeve External Diameter (mm) | 1.10 |
| | Sleeve Internal Diameter (mm) | 0.82 |
| Core | Triptorelin Acetate Content (mg/mg) | 0.486 |
| | Mean Dose (mg) | 9.5 |
| | Mean Purity (%) | 97.8 |
| | Implant Core Loading in Triptorelin Acetate (%) | 57.2 |

EXAMPLE 8

Polymeric Core in Polymeric Sleeve Manufacture Results 4

Six implants prepared according to Example 4 were selected, having the properties set out in Table 4, below.

TABLE 4

| | 4.2 mg triptorelin acetate polymeric core in 0.87 mm sleeve | |
|---|---|---|
| Sleeve | Sleeve Length (mm) | 26.3 |
| | Sleeve External Diameter (mm) | 0.87 |
| | Sleeve Internal Diameter (mm) | 0.70 |
| Core | Triptorelin Acetate Content (mg/mg) | 0.352 |
| | Mean Dose (mg) | 4.2 |
| | Mean Purity (%) | 97.4 |
| | Implant Core Loading in Triptorelin Acetate (%) | 41.4 |

EXAMPLE 9

Polymeric Core in Polymeric Sleeve Manufacture Results 5

Six implants prepared according to Example 4 were selected, having the properties set out in Table 5, below.

TABLE 5

| | 6.2 mg triptorelin acetate polymeric core in 1.08 mm sleeve | |
|---|---|---|
| Sleeve | Sleeve Length (mm) | 26.2 |
| | Sleeve External Diameter (mm) | 1.08 |
| | Sleeve Internal Diameter (mm) | 0.90 |
| Core | Triptorelin Acetate Content (mg/mg) | 0.345 |
| | Mean Dose (mg) | 6.2 |

TABLE 5-continued

| | 6.2 mg triptorelin acetate polymeric core in 1.08 mm sleeve | |
|---|---|---|
| | Mean Purity (%) | 97.5 |
| | Implant Core Loading in Triptorelin Acetate (%) | 40.6 |

EXAMPLE 10

Polymeric Core in Polymeric Sleeve Manufacture Results 6

Six implants prepared according to Example 4 were selected, having the properties set out in Table 6, below.

TABLE 6

| | 4.1 mg triptorelin acetate polymeric core in 0.85 mm sleeve | |
|---|---|---|
| Sleeve | Sleeve Length (mm) | 26.1 |
| | Sleeve External Diameter (mm) | 0.85 |
| | Sleeve Internal Diameter (mm) | 0.65 |
| Core | Triptorelin Acetate Content (mg/mg) | 0.394 |
| | Mean Dose (mg) | 4.1 |
| | Mean Purity (%) | 97.6 |
| | Implant Core Loading in Triptorelin Acetate (%) | 46.3 |

EXAMPLE 11

Polymeric Core in Polymeric Sleeve Manufacture Results 7

Six implants, prepared according to Example 4 were selected, having the properties set out in Table 7, below.

TABLE 7

| | 4.9 mg triptorelin acetate polymeric core in 0.85 mm sleeve | |
|---|---|---|
| Sleeve | Sleeve Length (mm) | 26.1 |
| | Sleeve External Diameter (mm) | 0.85 |
| | Sleeve Internal Diameter (mm) | 0.65 |
| Core | Triptorelin Acetate Content (mg/mg) | 0.464 |
| | Mean Dose (mg) | 4.9 |
| | Mean Purity (%) | 97.7 |
| | Implant Core Loading in Triptorelin Acetate (%) | 54.6 |

EXAMPLE 12

Triptorelin Core in Sleeve Manufacture Method

Examples 12 to 16 relate to the preparation of implants according to the invention, comprising a triptorelin acetate core in a polymeric tubular sleeve of PLGA.

Forty parts water for injection and 60 parts triptorelin acetate were weighed in two separated containers which were connected by way of a valve. A pump was used to create a vacuum in the triptorelin acetate container. The syringes were brought into contact and the water was sucked into the vacant spaces between the powder particles.

The gel formed by water and triptorelin acetate was homogenised by mixing.

The resulting triptorelin acetate in water gel was filled into a sleeve prepared according to Example 3. The sleeve was weighted before and after filling to confirm that the correct amount of triptorelin acetate in water was dosed.

The triptorelin acetate and water loaded inside the tube was dried in two stages. The mixture was incubated for 2-48 h at 20-30° C. and atmospheric pressure to produce a conformational change and thereafter was dried 6 h-24 h under vacuum to reduce the water content.

EXAMPLE 13

Triptorelin Core in Sleeve Manufacture Results 1

Six implants prepared according to Example 12 were selected, having the properties set out in Table 8, below.

TABLE 8

| 6.3 mg triptorelin acetate core in 0.85 mm sleeve | | |
|---|---|---|
| Sleeve | Sleeve Length (mm) | 26 |
| | Sleeve External Diameter (mm) | 0.85 |
| | Sleeve Internal Diameter (mm) | 0.65 |
| Core | Mean Dose (mg) | 6.3 |
| | Mean Purity (%) | 98.6 |

EXAMPLE 14

Triptorelin Core in Sleeve Manufacture Results 1

Six implants prepared according to Example 12 were selected, having the properties set out in Table 9, below.

TABLE 9

| 10.0 mg triptorelin acetate core in 1.10 mm sleeve | | |
|---|---|---|
| Sleeve | Sleeve Length (mm) | 26 |
| | Sleeve External Diameter (mm) | 1.10 |
| | Sleeve Internal Diameter (mm) | 0.85 |
| Core | Mean Dose (mg) | 10.0 |
| | Mean Purity (%) | 98.4 |

EXAMPLE 15

Triptorelin Core in Sleeve Manufacture Results 1

Six implants prepared according to Example 12 were selected, having the properties set out in Table 10, below.

TABLE 10

| 6.3 mg triptorelin acetate core in 1.1 mm sleeve | | |
|---|---|---|
| Sleeve | Sleeve Length (mm) | 26.0 |
| | Sleeve External Diameter (mm) | 1.10 |
| | Sleeve Internal Diameter (mm) | 0.82 |
| Core | Mean Dose (mg) | 6.3 |
| | Mean Purity (%) | 98.6 |

EXAMPLE 16

Triptorelin Core in Sleeve Manufacture Results 1

Six implants prepared according to Example 12 were selected, having the properties set out in Table 11, below.

TABLE 11

| 7.2 mg triptorelin acetate core in 1.2 mm sleeve | | |
|---|---|---|
| Sleeve | Sleeve Length (mm) | 28 |
| | Sleeve External Diameter (mm) | 1.2 |
| | Sleeve Internal Diameter (mm) | 0.8 |

TABLE 11-continued

| 7.2 mg triptorelin acetate core in 1.2 mm sleeve | | |
|---|---|---|
| Core | Mean Dose (mg) | 7.2 |
| | Mean Purity (%) | 98.8 |

EXAMPLE 17

Process of Twin Extrusion

A PLGA 85:15 in powder was first extruded in pellets. About 600 g of PLGA powder were extruded and 586.88 g were recovered in pellets (corresponding to a yield of 86%). Pellets were variable.

The extrusion parameter were as follows:

| | | Specifications | |
|---|---|---|---|
| Parameters | Target Value | Max | Min |
| Temperature zone 1 | 148° C. | 155° C. | 125° C. |
| Temperature zone 2 | 148° C. | 155° C. | 125° C. |
| Temperature zone 3 | 155° C. | 175° C. | 145° C. |
| Temperature zone 4 | 130° C. | 145° C. | 115° C. |
| Screw speed | 30 tr/min | 45 tr/min | 25 tr/min |
| Humidity | 45 | 75 | 15 |
| Pressure | / | 325 | / |
| Torque | / | 20 | / |
| Stretching speed | / | 40 | / |
| Oxygen | / | 40 | 10 |
| Length cut | 1 mm | / | / |
| Diameter | 1000 μm | 1500 μm | 500 μm |
| Bath Temperature | 20° C. | 23° C. | 17° C. |
| Feed Temperature | / | 27° C. | 17° C. |

The samples were produced with a specific set of equipments put in series in a single production line, a core extruder and a tubular coating/deposition system.

EXAMPLE 18

PLGA/Triptorelin Acetate Pellets Core Containing 34% of Triptorelin Acetate

This experiment was performed with PLGA and triptorelin acetate pellets (PLGA+active substance). The process of the triptorelin acetate concentration in pellets was about 34%.
Process Parameters:

| Parameters | Real value |
|---|---|
| Core extrusion A (Core) | |
| Temperature Zone 1 (° C.) | 130 |
| Temperature Zone 2 (° C.) | 130 |
| Temperature Zone 3 (° C.) | 130 |
| Material Temperature (° C.) | 130 |
| Material Pressure (bar) | 105 |
| Screw speed (rpm) | 8 |
| Screw torque (m/N) | 64.7 |
| Coating/deposition system B (Core) | |
| Temperature Zone 1 (° C.) | 140 |
| Temperature Zone 2 (° C.) | 150 |
| Temperature Zone 3 (° C.) | 140 |
| Material Temperature (° C.) | 145 |
| Material Pressure (bar) | 45 |
| Screw speed (rpm) | 20 |
| Screw torque (m/N) | |
| Carousel speed (m/min) | |

The two parts, core and shell showed a high adhesion and remained stuck together.

EXAMPLE 19

Polymeric Core and Polymeric Core in Polymeric Sleeve In Vitro Release Method

Examples 19 and 20 relate to in vitro studies of the polymeric core of Example 2 and a polymeric core in polymeric sleeve of Example 6.

The following procedure was used for in vitro release tests of implants according to Examples 2 and 6: The apparatus comprised a USP I (basket system) dissolution bath modified, connected to an auto sampler (MAXIMIZER™) with printer for data register on-line and a spectrophotometer UV-Vis with multicell system thermostatized by a programmable recirculating bath. The recirculating circuit of this bath included a 2 L glass where the release medium used in the second part of the assay was maintained. The spectrophotometer was connected to a PC that executed the CHEMSTATION™ software and controlled the sampling, analysis and bath conditions during the assay.

Further conditions were as set out below.

Temperature gradient: 56 hours at 37° C., increase up to 55° C. in 24 hours and 55° C. until the end.

Release medium: PBS pH=7.4 for 44 hours. Then eight transfers (one each 4 hours): consisting of extraction of 25 ml of PBS medium and introduction of preheated 20 mM Lactic acid pH=3. After these transfers the release medium was maintained. Both media were degassed prior to use.

Stirring rate: 75 rpm.

Dissolution medium volume: 100 ml.

Duration: 7 days for implants/10 days for microtube (not completely defined).

Analysis on-line: UV-Vis (280 nm).

EXAMPLE 20

Polymeric Core and Polymeric Core in Polymeric Sleeve In Vitro Release Results

The in vitro release profile of a polymeric core of Example 2 and an implant of Example 6 were obtained according to the procedure of Example 19. The in vivo release profile is shown in FIG. 1.

The in vitro release profile is markedly slower when the polymeric core of triptorelin acetate and PLGA is covered with a polymeric sleeve of PLGA than when it is not covered.

EXAMPLE 21

Polymeric Core in Polymeric Sleeve In Vivo Method

Examples 21 to 22 relate to in vivo studies of implants according to the invention, comprising a polymeric core of triptorelin acetate and PLGA in a polymeric tubular sleeve of PLGA.

The following procedure was used for in vivo tests of implants according to the invention.

Six male Beagle dogs were selected and one implant was administered to each dog by subcutaneous route in the back of the neck.

An implant produced according to Example 4 was placed by hand in the device for administration by injection. The implant and device were exposed to gamma-irradiation above 25 above 25 kGy. The device in the form of a syringe weighed before and after administration in order to verify complete administration.

Blood samples were obtained through the cephalic vein. The 6 month sampling schedule was prepared as follows: before injection (time 0), 15 and 30 min, 1, 2, 4, 8 and 12 h and then 1, 2, 3, 7, 10, 15, 20, 24, 27, 30, 37, 44, 51, 60, 69, 76, 83, 90, 105, 120, 135, 150, 165, 180 d. If triptorelin concentrations were already detected and dogs were castrated, samples were taken once every 14 to 16 d from this time until triptorelin levels were repeatedly below detectable levels and testosterone levels were above the limit of castration.

Samples were withdrawn in a syringe containing an anticoagulant and a preservative. The content of each syringe was gently mixed. The blood samples remained in a cold water bath until centrifuged (1600 g for 20 min at 4° C.). Finally, 1 ml of the plasma was transferred into polypropylene cryotubes for testosterone analysis and the remaining plasma was transferred into polystyrene tubes for triptorelin analysis. They were rapidly frozen below −20° C., at which temperature they remained until analysis.

The triptorelin plasma concentrations were determined by means of the RIA method. This method, previously validated, involves the preparation of calibrated standard curves and the inclusion of quality control samples. The limit of quantification is 20 pg·ml$^{-1}$.

In addition, the concentration of testosterone in dog plasma samples was analysed after the on-line solid phase extraction of 0.3 ml of dog plasma samples coupled to LC-MS/MS using the testosterone trideuterated as internal standard and female dog blank plasma so as not to interfere with the basal testosterone levels present in healthy male dogs. This method, previously validated, involves the preparation of standard calibration curves and the inclusion of quality control samples from female dog blank plasma so as not to interfere with the basal testosterone levels present in male dogs.

The implants of Examples 6 to 8 above were administered to dogs in corresponding Examples 22 to 24.

Administration was via needles having an external diameter of 1.2 or 1.4 mm, or by way of a Retroinjector.

EXAMPLE 22

Polymeric Core in Polymeric Sleeve In Vivo Results 1

Figure 2:
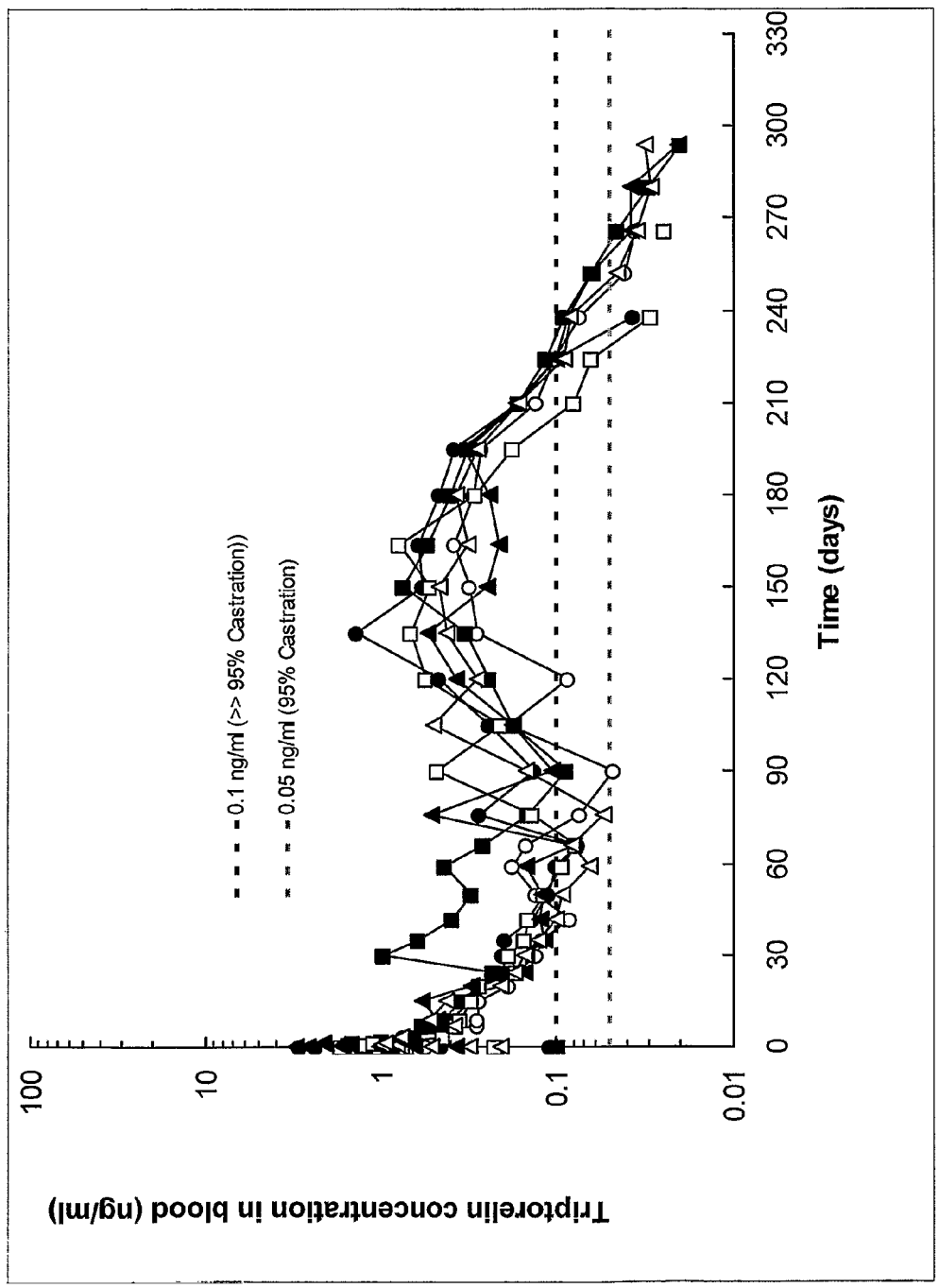
FIG. 2: shows triptorelin concentration over time in six dogs following injection of an implant prepared according to Example 5 (5.9 mg triptorelin acetate polymeric core in 1.1 mm sleeve).

Implants of Example 6 were injected into six dogs according to the procedure of Example 21. The in vivo release profile is shown in FIG. 2.

After the subcutaneous administration, drug plasma levels were quantifiable for at least 8 months in all dogs. The mean±S.D. triptorelin plasma level at 6 months was 0.34±0.08 ng/ml. The plot of plasma levels versus sampling times showed very good burst control (mean±SD $C_{max}$ of 1.9±0.87 ng/ml) at a median $t_{max}$ of 4 hours. Then, after a slight decrease in triptorelin levels up to 30 days, a zero order release was observed to 90 days (around median $C_{30-90d}$ value of 0.127 ng/ml). Peak plasma levels were observed in all dogs between 90 and 180 days, with triptorelin concentrations ranging from 0.379 to 1.395 ng/ml.

EXAMPLE 23

Polymeric Core in Polymeric Sleeve In Vivo Results 2

Figure 3:
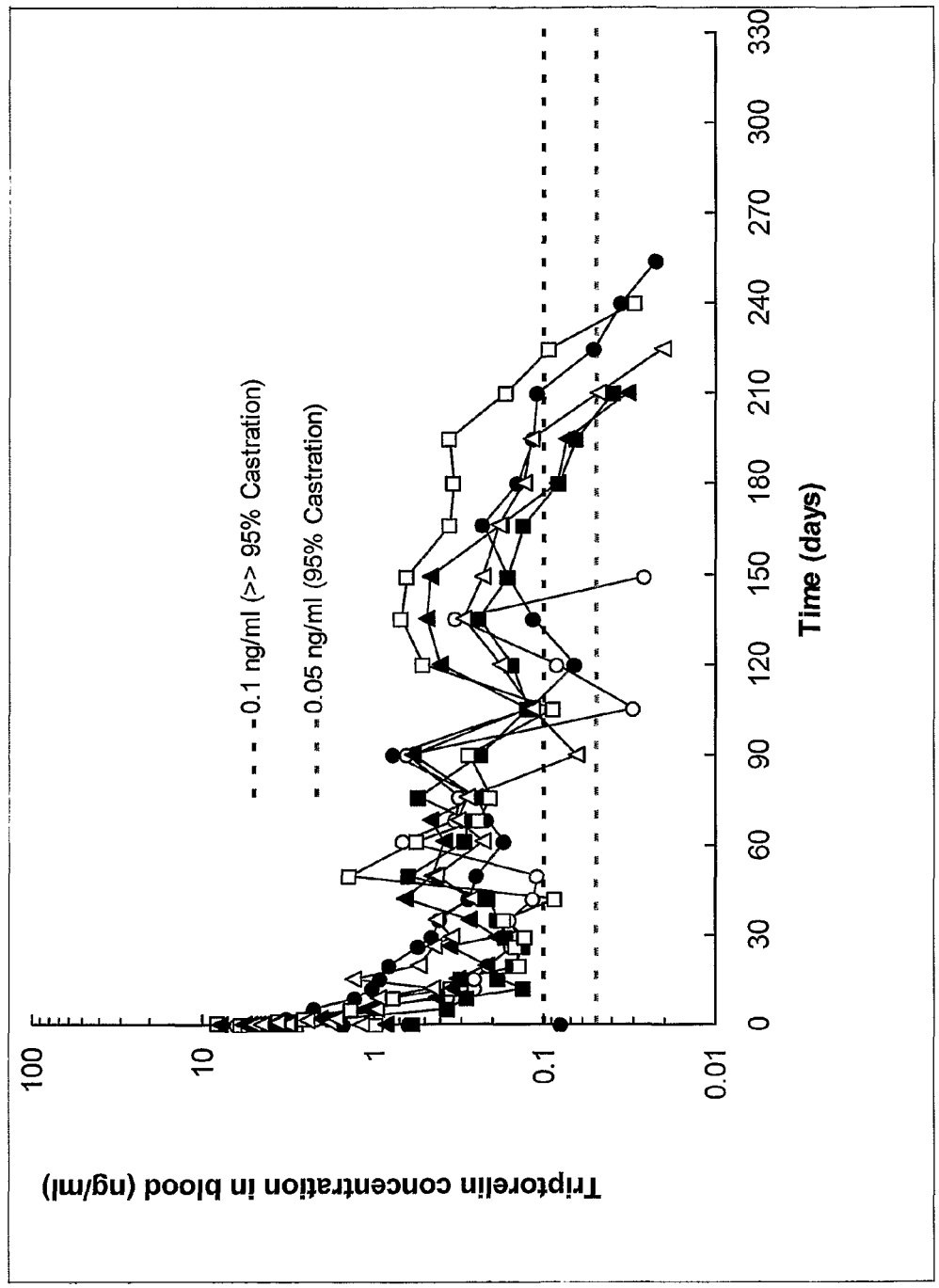
FIG. 3: shows triptorelin concentration over time in six dogs following injection of an implant prepared according to Example 6 (6.4 mg triptorelin acetate polymeric core in 0.85 mm sleeve).

Implants of Example 7 were injected into six dogs according to the procedure of Example 21. The in vivo release profile is shown in FIG. 3.

After the subcutaneous administration, drug plasma levels were quantifiable for at least 7 months in five out of the six dogs. The mean±S.D. triptorelin plasma level at 6 months was 0.13±0.11 ng/ml. The plot of plasma levels versus sampling times showed good burst control (mean±SD $C_{max}$ of 6.0±1.6 ng/ml) at a median $t_{max}$ of 2.5 hours. Then, after a slight decrease in triptorelin levels up to 30 days, a pseudo zero order release was observed to 90 days (around median $C_{30-90d}$ value of 0.341 ng/ml). Subsequently, levels decreased rapidly up to 105 days (from mean $C_{90d}$ value of 0.42 ng/ml to mean $C_{105d}$ value of 0.10 ng/ml). Finally, peak plasma levels were observed in all dogs between 105 and 150 days, with triptorelin concentrations ranging from 0.226 to 0.678 ng/ml.

EXAMPLE 24

Polymeric Core in Polymeric Sleeve In Vivo Results 3

Figure 4:
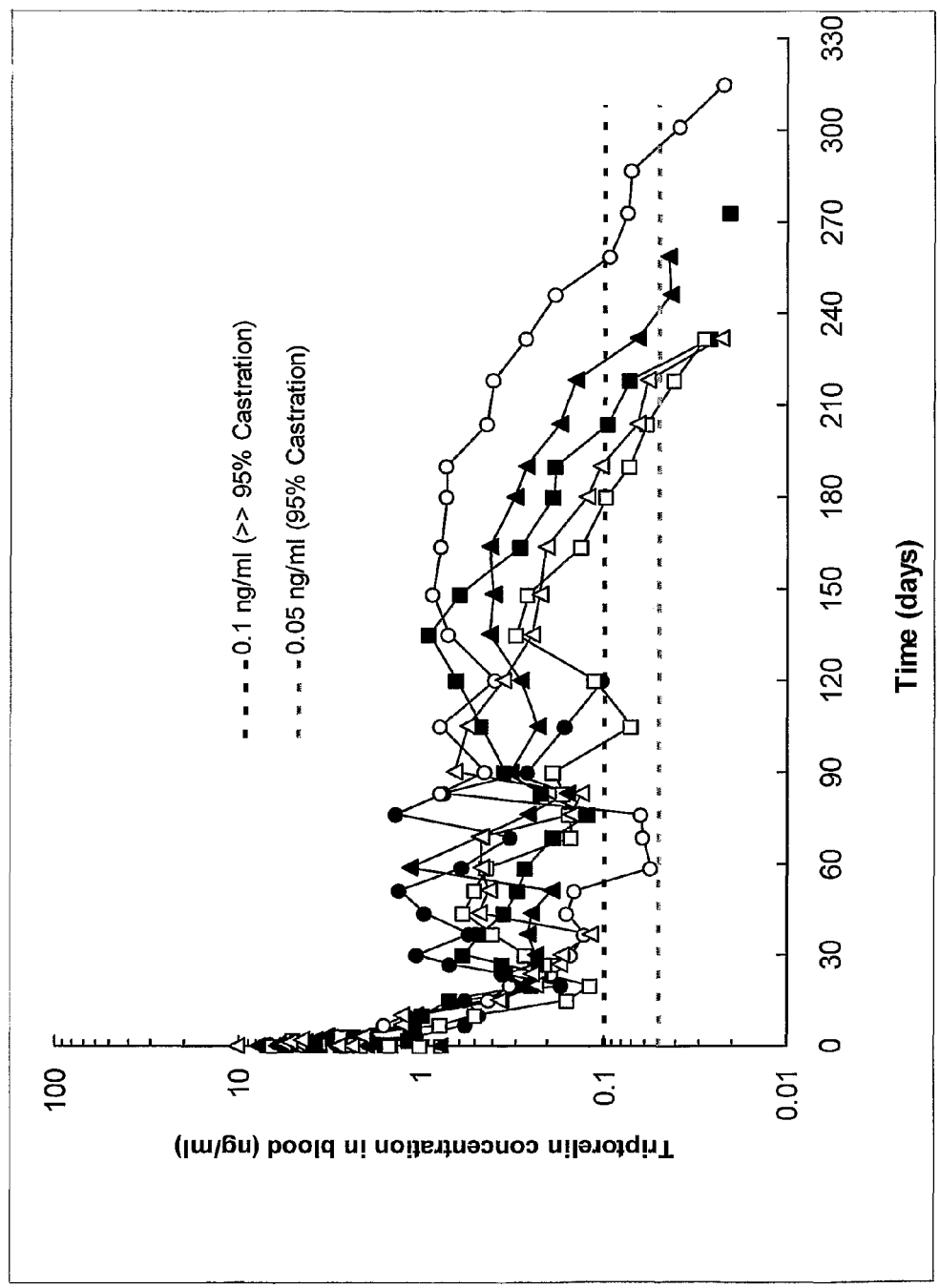
FIG. 4: shows triptorelin concentration over time in six dogs following injection of an implant prepared according to Example 7 (9.1 mg triptorelin acetate polymeric core in 1.1 mm sleeve).

Implants of Example 8 were injected into six dogs according to the procedure of Example 21. The in vivo release profile is shown in FIG. 4.

After the subcutaneous administration, drug plasma levels were quantifiable for at least around 8 months in five out of the six dogs. The mean±S.D. triptorelin plasma level at 6 months was 0.24±0.26 ng/ml. The plot of plasma levels versus sampling times showed good burst control (mean±SD $C_{max}$ of 7.4±1.7 ng/ml) at a median $t_{max}$ of 4 hours. Then, after a slight decrease of triptorelin levels up to 20 days, a pseudo zero order release was observed to 150 days (around median $C_{20-150d}$ value of 0.36 ng/ml).

EXAMPLE 25

Triptorelin Core in Polymeric Sleeve In Vivo Results 1

Examples 25 and 26 relate to in vivo studies of implants according to the invention, comprising a triptorelin core in a polymeric tubular sleeve of PLGA.

Figure 5:
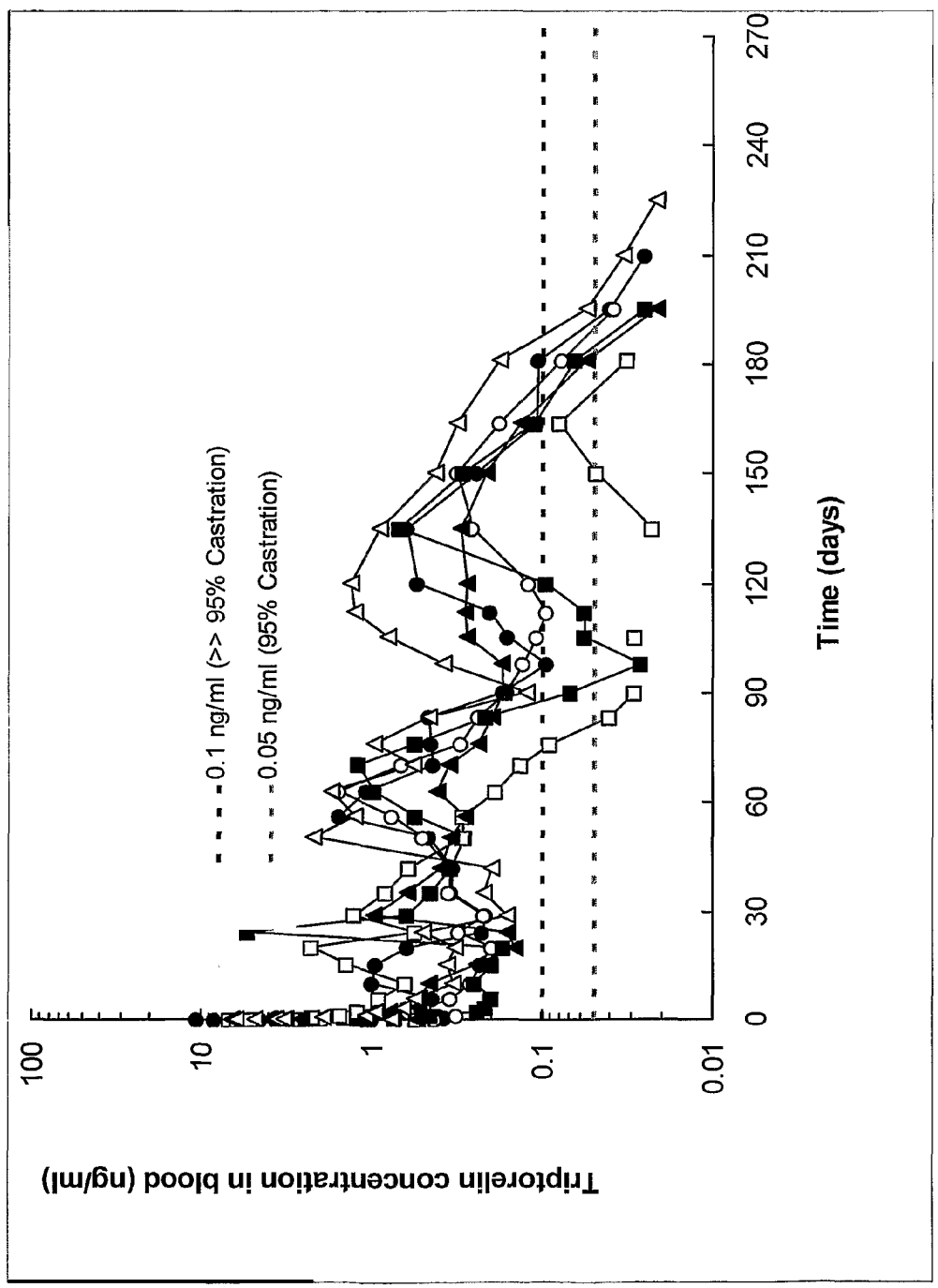
FIG. 5: shows triptorelin concentration over time following injection of the implant of Example 13 (6.3 mg triptorelin acetate core in 0.85 mm sleeve) in six dogs.

Implants of Example 13 were injected into six dogs according to the procedure of Example 21. The in vivo release profile is shown in FIG. 5.

After the subcutaneous administration, drug plasma levels were quantifiable for at least 6 months in all dogs. The mean±S.D. triptorelin plasma level at 6 months was 0.09±0.05 ng/mL. The plot of plasma levels versus sampling times showed good burst control (mean±SD $C_{max}$ of 6.4±2.3 ng/ml) at a median $t_{max}$ of 1 hour. Then, after a fast decrease of triptorelin levels from 1 hour to 12 hours, a zero order release was observed to 40 days (around median $C_{0.5-40d}$ value of 0.633 ng/ml). Two peak plasma levels were observed in the majority of dogs between 40 and 90 days and from 98 to 180 days, with triptorelin concentrations ranging from 0.414 to 2.164 ng·ml$^{-1}$ and from 0.307 to 1.311 ng/ml, respectively.

EXAMPLE 26

Triptorelin Core in Polymeric Sleeve In Vivo Results 2

Figure 6:
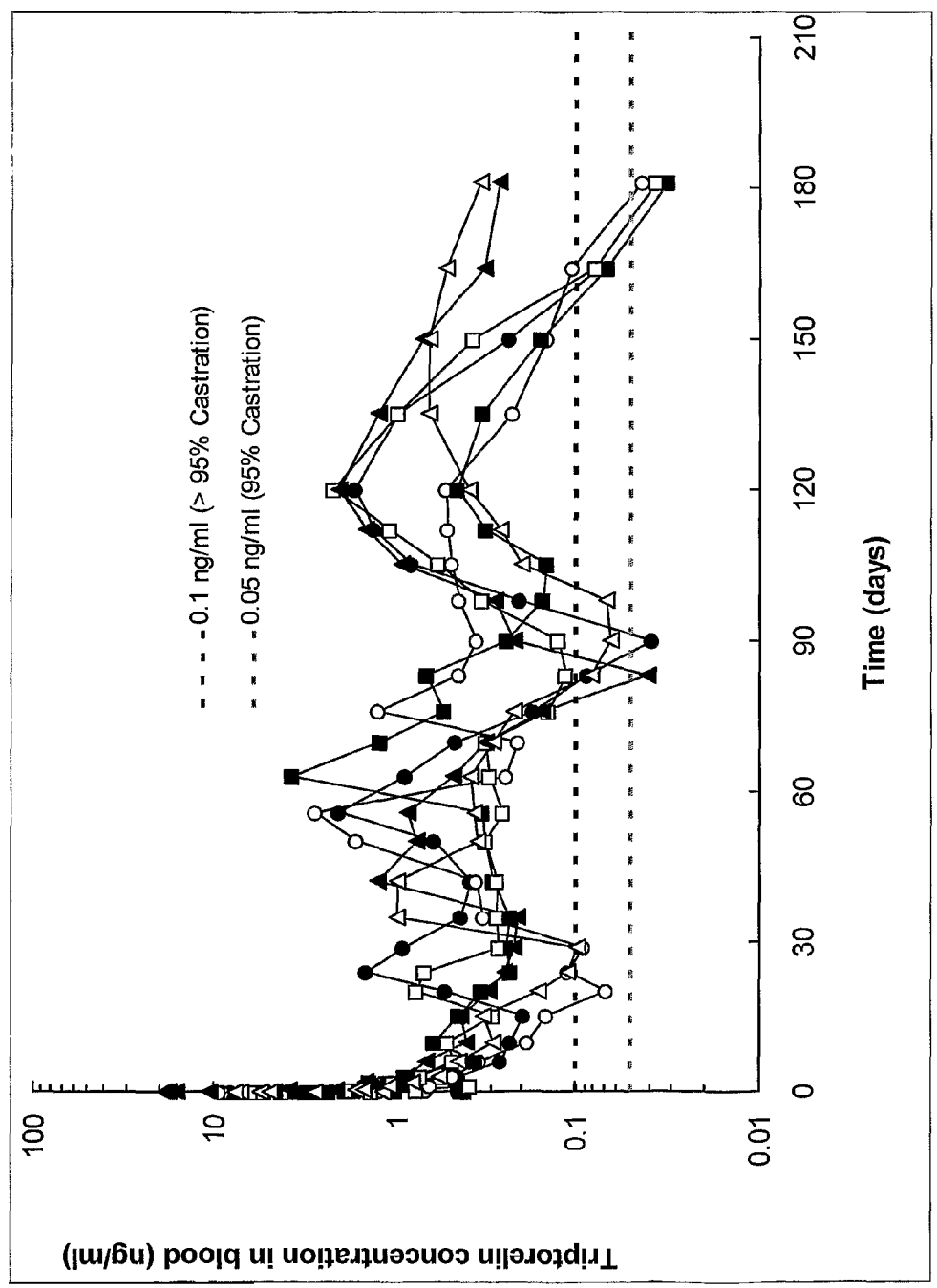
FIG. 6: shows triptorelin concentration over time following injection of the implant of Example 14 (10.0 mg triptorelin acetate core in 1.10 mm sleeve) in six dogs.

Implants of Example 14 were injected into six dogs according to the procedure of Example 21. The in vivo release profile is shown in FIG. 6.

After the subcutaneous administration, drug plasma levels were quantifiable for at least 6 months in five out of the six dogs. The mean±S.D. triptorelin plasma level at 6 months was 0.12±0.15 ng/ml. The plot of plasma levels versus sampling times showed good burst control (mean±SD $C_{max}$ of 8.9±5.0 ng/ml) at a median $t_{max}$ of 1 hour. Then, after a rapid decrease in triptorelin levels from 1 hour to 1 day, a zero order release was observed to 30 days (around median $C_{0.5-30d}$ value of 0.552 ng/ml). After that, two peak plasma levels were observed in the majority of dogs between 30 and 90 days and from 90 to 180 days, with triptorelin concentrations ranging from 0.323 to 3.709 ng·ml$^{-1}$ and from 0.457 to 2.247 ng/ml, respectively.

The invention claimed is:

1. An implant comprising:
    an elongated biodegradable polymeric core comprising at least one GnRH analogue, wherein said GnRH analogue is triptorelin acetate;
    an elongated biodegradable polymeric sleeve outside of the core;
    the core being exposed through an opening in the sleeve proximate at least one end of the implant,
        wherein the implant is capable of controlled and sustained release of the GnRH analogue, and
        said implant is prepared by a method comprising the steps of:
        (a) preparing a polymeric sleeve,
        (b) preparing a 40% to 80% (w/w) solution of triptorelin acetate in water,
        (c) placing the solution in the sleeve,
        (d) incubating the solution at 20 to 30° C. for 2 to 48 hours and
        (e) drying under vacuum for 6 to 24 hours.

2. The implant of claim 1, wherein the controlled and sustained release occurs at least in part via release of triptorelin acetate through the opening in the sleeve.

3. The implant of claim 1, wherein the controlled and sustained release occurs at least in part via release of triptorelin acetate through the sleeve, as the sleeve and core degrades.

4. The implant of claim 1, wherein the polymeric core is 30 to 90% by weight triptorelin acetate relative to the total weight of the polymeric core.

5. The implant of claim 4, wherein the polymeric core is 35 to 65% by weight triptorelin acetate relative to the total weight of the polymeric core.

6. The implant of claim 1, wherein the polymeric core and the polymeric sleeve comprise the same polymer.

7. The implant of claim 6, wherein the polymer is poly (lactide-co-glycolide) acid (PLGA).

8. The implant of claim 7, wherein the ratio of lactic acid to glycolic acid in the PLGA is within the range of 70:30 to 90:10.

9. The implant of claim 8, wherein the ratio of lactic acid to glycolic acid in the PLGA is 85:15.

10. The implant of claim 1, wherein the implant is capable of sustained release for at least 3 months.

11. The implant of claim 10, wherein the implant is capable of sustained release for at least 6 months.

12. The implant of claim 1, wherein the implant comprises 0.5 to 50 mg of triptorelin acetate.

13. The implant of claim 12, wherein the implant comprises 2 to 20 mg of triptorelin acetate.

14. The implant of claim 13, wherein the implant comprises 5 mg of triptorelin acetate.

15. The implant of claim 13, wherein the implant comprises 6 mg of triptorelin acetate.

16. The implant of claim 13, wherein the implant comprises 7 mg of triptorelin acetate.

17. The implant of claim 13, wherein the implant comprises 8 mg of triptorelin acetate.

18. The implant of claim 13, wherein the implant comprises 9 mg of triptorelin acetate.

19. The implant of claim 13, wherein the implant comprises 10 mg of triptorelin acetate.

20. The implant of claim 1, wherein the implant has an axial length of between 2 and 3 cm.

21. The implant of claim 20, wherein the implant has an axial length of 2.6 cm.

22. The implant of claim 1, wherein the implant has a ratio of the diameter to axial length of between 1:20 and 1:40.

23. The implant of claim 22, wherein the implant has a ratio of the diameter to axial length of 1:30.

24. The implant of claim 7, wherein the PLGA has a molecular mass of at least 60 kDa.

25. The implant of claim 7, wherein the PLGA has a molecular mass of at least 100 kDa.

26. An implant comprising:
   (a) a polymeric sleeve having at least one open end, and
   (b) a core within the sleeve comprising triptorelin acetate,
      wherein the implant comprises a void between the sleeve and the core,
      wherein the implant is obtained by manual insertion of the core into the polymeric sleeve.

27. The implant of claim 26, wherein the polymeric sleeve is a polymer of poly(lactide-co-glycolide) acid (PLGA).

28. A method for preparing an implant, comprising the steps of:
   (a) preparing a polymeric sleeve,
   (b) preparing a 40% to 80% (w/w) solution of triptorelin acetate in water,
   (c) placing the solution in the sleeve,
   (d) incubating the solution at 20 to 30° C. for 2 to 48 hours and
   (e) drying under vacuum for 6 to 24 hours.

29. The implant of claim 1, wherein the implant comprises a void between the sleeve and the core.

30. An implant comprising:
   an elongated biodegradable polymeric core comprising at least one GnRH analogue,
      wherein said GnRH analogue is triptorelin acetate;
      an elongated biodegradable polymeric sleeve outside of the core,
      wherein said the polymeric sleeve is a polymer of poly(lactide-co-glycolide) acid (PGLA);
   the core being exposed through an opening in the sleeve proximate at least one end of the implant,
      wherein said implant has an external diameter of 0.70 mm to 1.2 mm;
      wherein said implant has an axial length of 2.6 cm to 4 cm;
      wherein the implant is capable of controlled and sustained release of the GnRH analogue.

31. The implant of claim 30, wherein said implant has an external diameter of 0.70 mm, 0.80 mm, 0.85 mm, 0.87 mm, 0.90 mm, 0.95 mm, 1.0 mm, 1.08 mm, 1.1 mm, or 1.2 mm.

32. The implant of claim 30, wherein said implant has an axial length of 2.5, 2.6, 2.7, or 2.8 cm.

33. The implant of claim 30, wherein said biodegradable polymeric sleeve has a thickness of 280 μm to 400 μm.

* * * * *